(12) United States Patent
Jensen et al.

(10) Patent No.: US 6,855,354 B2
(45) Date of Patent: Feb. 15, 2005

(54) FREEZE CONCENTRATION PROCESS

(75) Inventors: Claude Jarakae Jensen, Cedar Hills, UT (US); Brett J. West, Orem, UT (US); Robert V. Ogden, Cedar Hills, UT (US); Stephen P. Story, Alpine, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 10/044,158

(22) Filed: Jan. 11, 2002

(65) Prior Publication Data

US 2003/0099731 A1 May 29, 2003

Related U.S. Application Data

(60) Provisional application No. 60/268,305, filed on Feb. 13, 2001.

(51) Int. Cl.⁷ .............................................. A61K 35/78
(52) U.S. Cl. ...................... 424/777; 424/725; 426/384
(58) Field of Search ................................ 426/384, 524; 424/195.1, 725, 777

(56) References Cited

U.S. PATENT DOCUMENTS 4,463,025 A * 7/1984 Strobel ....................... 426/599
6,254,913 B1 * 7/2001 Wadsworth et al.

OTHER PUBLICATIONS

Lumpur, K. Morinda Achieves Phenomenal Sales of Tahitian Noni Juice; Malaysian National News Agency, Jul. 1999, p. 1.*

* cited by examiner

*Primary Examiner*—Patricia Leith
(74) *Attorney, Agent, or Firm*—Kirton & McConkie; Michael F. Krieger

(57) ABSTRACT

The use of an improved method for freeze concentration is disclosed. The method provides for first freezing components of a pulpy slurry of *Morinda citrifolia*. More dilute components are extracted after the initial freezing. A secondary freezing process at a lower temperature allows more concentrated portions of a *Morinda citrifolia* slurry to be removed. Flavor and therapeutic oils remain in the resulting concentrate for improved flavor and health benefits.

8 Claims, 2 Drawing Sheets

FREEZE CONCENTRATION PROCESS

This application claims priority to U.S. Provisional Patent Application Ser. No. 60/268,305 filed Feb. 13, 2001 to Claude Jarakae Jensen entitled "FREEZE CONCENTRATION PROCESS."

BACKGROUND

1. Importance of Fruits in Human Diet

As "accessory foods," fruits have an important role in the human diet. They add a variety of color, taste, and texture to meals and snacks. Nutritionally, fruits provide significant amounts of several vitamins and are major contributors of essential minerals.

Most fresh fruits contain 75 to 95 percent water. They are low in protein but generally contain substantial quantities of carbohydrates, including varying proportions of dextrose, fructose, sucrose, and starch, depending on the type of fruit and its maturity.

Dehydration is probably the oldest method of preservation of fruits. Sun-dried fruits antedate the use of fire for cooking and the roots of the modern dehydrated, dehydrofrozen, and granulated fruit industry can be traced back to this oldest method of fruit processing.

Fermentation was another popular mode of fruit juice processing and preservation. Fermented beverages such as beer, wine, cider, brandy, cordials, and nectars have since given way to fruit juices, punches, nectars, sport drinks, and concentrates. These products could be canned, frozen, dried, powdered, or concentrated.

Chemical preservation of whole, sliced, or sectioned fruit by soaking them in honey or sugar syrup or by use of vinegar or wine represents one of the oldest methods of fruit processing and preservation. Today, these products have been replaced by a variety of fruit preserves, jams, marmalades, glazes, jellies, fruit butters, sauces, and pickles.

Thus, the leading methods of processing fruits have shifted continuously through the centuries from sun-drying and sugar and chemical preservation towards modern day, technology-oriented processing methods such as canning, artificial dehydration, concentration, radiation, and freezing, or combinations of one or more of these methods. With that shift, the consumption pattern of fruits has also changed. The percentage of fruits processed as compared to those eaten fresh has steadily increased. This general trend appears to have been due to improvements in varieties of fruits for processing, horticultural practices and production of fruits especially suitable for processing, mechanical harvesting of fruits, techniques for processing large volumes of fruits, containers more suitable for processed fruit, extending the shelf-life of processed fruits, raising the standards and nutritional value of processed fruits, and more attention to marketing of processed fruits, especially for export purposes.

2. Fruit Juice Concentration

The common liquid foods encountered in everyday life are mostly aqueous solutions and/or suspensions. Those prominent in our daily life include fruit juices, soups, tea, coffee, milk, beer, and wines. The solid content of most liquid foods is low, usually in the range of 8 to 16 percent. Oftentimes it is expensive to package, store, and ship "single-strength" liquids, and in many cases it is desirable to remove a part or all of the water from such liquids.

It is obvious that much of what the consumer eats and pays for in food is water. Water alone makes up 70 to 95 percent of the total cost of most products. Another aspect of water in frozen foods can be judged by the energy required for transportation.

Fruit juices are watery mixtures of mostly unstable volatile organic compounds. They are heat sensitive and their color and flavor deteriorate rapidly as processing temperatures are increased. Even at moderate temperatures, many of their components are unstable. At temperatures between 40 and 70° C., enzyme-catalyzed reactions can alter juice properties within a few minutes. In order to inactivate the enzymes, juices must be heat treated. At the same time, to obtain a quality product, it is essential to have sanitary conditions of high standards. Since it is the aroma volatile that give food product their wide variety of flavor sensations, even monic changes in aroma during concentration can greatly alter the sensory qualities of the final product.

Selective water removal processes commonly used in the food industry can be divided broadly into two classes: concentration and dehydration processes. The former includes processes that increase solids content to about 50 to 60 percent (still in liquid form) and the latter those that reduce water content to less than 10 percent and the final product is in solid form. The selection of any one of these processes for removing water from a food product is primarily governed by the physical properties of the form (liquid or solid), economics, and the desired quality of the final products.

A.) Concentration Processes

Concentration processes for fruit juices may be broadly classified based on whether removal of water involves a phase change. Processes which require a phase change include evaporation and distillation, pervaporation, and crystallization or freezing. In direct and reverse osmosis processes, phase change of solvent is not required. Maximum separation of water in evaporation and freezing processes is obtained at phase equilibrium. The rest are typical nonequilibrium processes and are based upon differences in velocity of equilibrium approach.

3. Evaporation and Distillation

Evaporation is defined as the removal by evaporation of a part of the solvent (usually water in case of food liquids) from a solution or dispersion of essentially nonvolatile solutes. The term "evaporation" is usually used when the resultant product is still in a liquid or semisolid state.

Evaporation is probably the oldest method of concentration known to mankind. Some of the most primitive methods of evaporation are still in use today. For example, the use of solar ponds is still an economical means of salt production. At present, evaporation is considered as the best developed, economically the most favorable, and the most widely used method for concentration of food liquids.

For food liquids whose quality is not determined by their aroma composition, evaporation may be conducted at the boiling point of the liquid. The quality of most food liquids, however, is primarily influenced by their aroma characteristics. Almost all aroma and flavor constituents of foods are low-boiling volatile compounds. Thus, they may be removed prior to effecting water removal or may be destroyed depending on their thermal stability. In evaporation processes where the liquid is to be concentrated fourfold or more, the loss of these compounds is almost directly proportional to the loss of vapor. Lower processing temperatures are, therefore, required for such food liquids. The boiling point of these liquids can be lowered by reducing the pressure. Such water removal at reduced pressure, and hence at reduced temperature, is known as vacuum evaporation.

Concentration of fruit juices by vacuum evaporation is, however, still a severe process. It is reported that when apple juice was concentrated by heating under the vacuum, the first 10 percent of the juice vaporized contained all the volatile flavoring constituents. Commercially, fruit juice concentrates are, therefore, produced by first stripping their aroma volatile in a distillation column, followed by concentration in a vacuum evaporator. The aroma concentrate is then added back to the concentrate of nonvolatile liquid to yield a flavorful product. A much simpler method to restore partly the quality of the final product is to add fresh juice to the concentrate. The resulting dilution with "cutback" of fresh juice to the concentrate makes it impractical to obtain products above fourfold the original strength.

Fruit juices contain both soluble (such as sugars and acids) and insoluble (such as fiber) components and, therefore, cannot be defined as "true solutions." In such a system, the thermodynamic properties of water deviate from those of pure water; therefore, the phase diagrams for pure water cannot be applied directly for the purpose of calculating energy requirements for the removal of water. To effect water removal, the total amount of energy input necessary is governed by the following factors: 1) the initial temperature of the feed; 2) operating pressure in a particular system; 3) the amount of water to be removed; 4) the effect of the solubles in solubles present in the feed on the thermodynamic properties of water; and 5) efficiency of a particular process design.

Computing such energy requirements requires knowledge of process design and the equipment used to achieve the desired degree of concentration. In simplistic terms, the minimum energy required to transform unit mass of saturated liquid water to saturated vapor (at a constant temperature and pressure) is equal to the enthalpy or the latent heat of vaporization.

Evaporation may be conducted in a batch or continues mode depending on the need. In the food industry, the latter type is more commonly used. Most vacuum evaporators consist of multistage units. The heating medium for each stage may be stem, water vapor from the previous stage, or both. When water vapor from the previous stage (boiling juice) is used as heating medium to evaporate water from juice at a lower temperature, the process is known as an "effect." As many as seven stages and four effects have been used to concentrate orange juice. Several aspects of the types of evaporators used in the food industry have been reviewed.

A.) Aroma Recovery in Evaporation Processes

The highly volatile constituents of fruits that are responsible for the characteristic aroma of the fruit juices are present in only trace amounts. Since these aroma compounds are, in general, more volatile than water, they may be lost either partly or completely if the vapor is discarded during concentration of fruit juices by evaporation. The "cutback" process is used to restore partly the quality of concentrated juice that was not suited for the production of concentrates other than citrus juices. With newer, improved technology, the volatile aromas can be recovered by removing them from either the feed before evaporation or from the vapor produced in the evaporator. These dilute aqueous aromas can then be concentrated by distillation or freeze concentration and are returned to the concentrate of non-volatile from the evaporator. Several reviews have described the aroma recovery systems available for the production of flavorful fruit juice concentrates.

SUMMARY AND OBJECTS OF THE INVENTION

The present invention is directed toward an improved method for concentrating *Morinda citrifolia* slurry. More specifically, the method comprises the use of freeze concentrating on pulpy products through the process of freezing various components of the slurry and the pulp contained within the slurry and then extracting the frozen components from the slurry. The method provides that the flavor and therapeutic values incorporated in the *Morinda citrifolia* slurry remain in the resulting concentrate. The method involves the chilling of the slurry to a temperature and pressure that allows crystals and constituents to be removed from the slurry and then further chilling the slurry to the temperature and pressure that produces crystals of the slurry that can then be removed.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE PREFERRED EMBODIMENTS

Freeze concentration involves partial freezing of the product and removal of the pure ice crystals, thus leaving behind all of the nonaqueous constituents in the concentrated phase. Although water constitutes more than 85 percent by weight of most fruit juices and other food liquids, its properties differ greatly from those of pure water under identical conditions. These properties are greatly influenced by the type and amount of dissolved solids in water.

Figure 1:
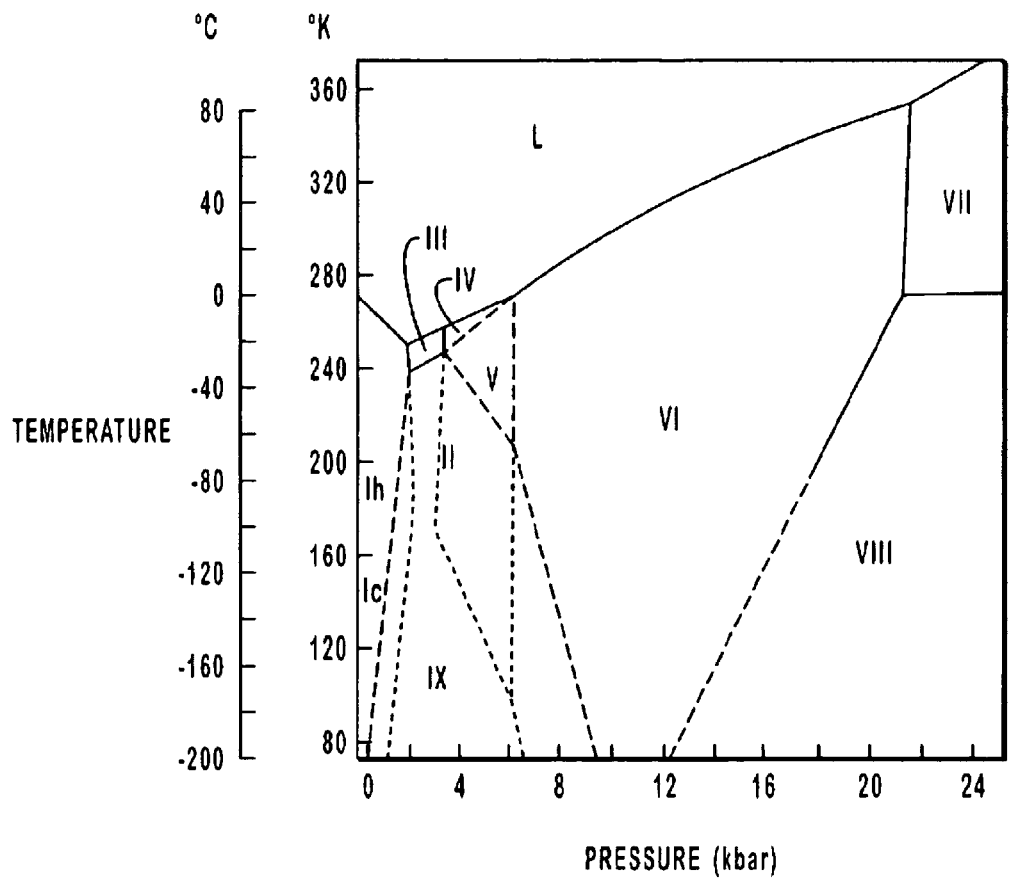
FIG. 1 shows a graph depicting the phase transition properties of water.

A simple phase diagram indicating the several physical states of water at equilibrium is shown. The equilibrium conditions between the solid, liquid, and gaseous states of water are temperature and pressure dependent. A state of equilibrium of ice, liquid water, and water vapor exists only at the triple point with a pressure of 4.579 mmHg and a temperature of 0.0099° C. (FIG. 1). Below the triple point, the ice is directly sublimed into a gaseous state. This forms the basis of the freeze-drying technology. As shown in FIG. 1, water can exist, under proper conditions of temperature and pressure, in 11 different physical states. These include one each for liquid and vapor phases, and nine different crystalline solid phases. The latter are the different high-pressure polymorphs of ice.

Separation by freezing is based on the difference in component concentrations between solid and liquid phases that are in equilibrium. The phase transitions that occur in true solutions can be analyzed fairly accurately based on the regularities of ice formation in nonstructural systems. However, for multicomponents of pseudosystems, many generalizations have to be made. The most important phase transitions in food products of plant origin that take place at lower temperatures are as follows: 1) crystallization and melting (including the eutectic phenomena); 2) vitrification; 3) glass (vitreous) transformation; 4) devitrification (crystallization) following glass transformation; 5) recrystallization preceding melting; and 6) antemelting.

The formulation of ice in a sample, diluted binary (two-phase) system is accompanied by: 1) the separation of water as pure ice crystals; 2) a progressive increase in the concentrations of the dissolved substance; and 3) a gradual decrease in the melting point of the concentrated solution. At eutectic temperature, both the unfrozen water phase and the substance dissolved in it crystallize simultaneously in a fixed relationship, forming a mixed conglomerate (hydrate). In multicomponent solutions, the dissolved solids crystalize out successively according to their eutectic temperatures. Unfrozen water is retained in the systems until the lowest eutectic temperature becomes saturated.

Fruit juices are not "true" solutions, since in addition to water, they contain a large number of soluble components. However, for reasons of simplicity, fruit juices are considered as pseudobinary systems where all substances dissolved in water are considered as one component.

Figure 2:
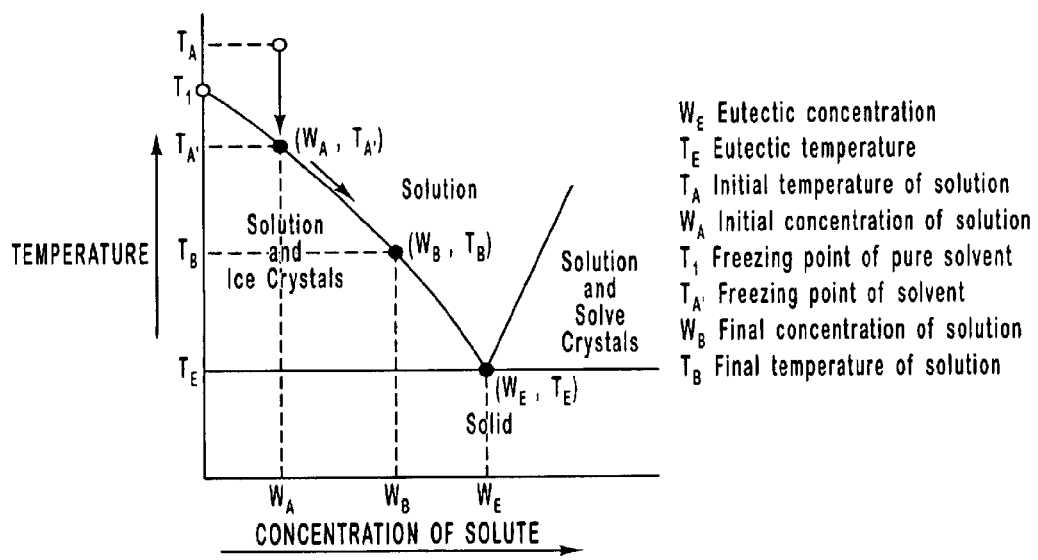
FIG. 2 shows a graph depicting a phase diagram of a binary mixture.

A simple phase diagram of binary mixture is shown in FIG. 2. If a binary mixture is cooled from its initial temperature $T_A$ under conditions allowing equilibrium to be attained, then a solid crystalline phase (pure ice crystals) begins to appear in liquid phase. This corresponds to composition $W_A$ and the freezing point $T_A^1$ in the phase diagram. Usually only one component in the binary mixture crystalizes out in a pure form. Theoretically, this allows a single-stage operation of the process, as compared to the incremental separation and multistage processes required in vapor-liquid separations.

At the initial freezing temperature ($T_A^1$) where the crystallization process begins, only small amounts of crystals are generated. As crystallization proceeds, the concentration of liquid water in the solution will decrease. The dissolved substances will be concentrated progressively in the liquid phase. This decreases the crystallization temperature of the remaining liquid; therefore, a lower operating temperature is required to effect further crystallization. At this stage, the liquid composition follows the line $[CW_A T_A^1)(W_B, T_B)]$ in the phase diagram. It is apparent that for higher conversions to the crystal phase, i.e., for effective ice separation, successively lower temperatures are required. At eutectic concentration ($W_E$) and temperature ($T_E$), the crystallizing solid has the same composition as the supernatant liquid. Thus, at the eutectic, both components crystallize out simultaneously. At this stage, removal of heat from the system converts more of the liquid phase to solid, but at a constant temperature.

Theoretically, the concentration process can only be applied to a concentration just below that of eutectic. However, in most cases, because of the problems connected with separating ice from a very viscous liquid (both because of concentration and low temperature), it must stop well below the eutectic. Generally, concentration can be carried to the point where the slurry at the prevailing low temperature becomes too thick to be pumped. With the commercially available equipment, it is possible to concentrate most fruit juices to about 50 percent solids content.

Concentration by freezing has several advantages over other concentration processes such as evaporation and reverse osmosis. Some of the advantages claimed are discussed below.

One of the obvious advantages of freeze concentration over evaporative methods is that the energy to freeze a unit of water is much less than that required to evaporate it. At any given process temperature, approximately one seventh as much heat must be withdrawn from a pound of water to freeze it as must be added to vaporize it as in evaporative processes. It is estimated that with their process, 1 kWh of energy input could produce approximately 70 to 80 pounds of ice. Similarly, since the object is to freeze the final product, considerably less cooling is required after processing and concentration. Substantial energy savings are, therefore, possible in many applications of freeze concentration as compared to the more conventional evaporation processes. Freezing processes can be designed to either utilize electricity as the sole energy source or to operate the process in an absorption cycle using waste heat at as low as 130 to 140° F. In many industrial applications, waste heat at these temperature levels has no value and it represents a disposal cost. Based on food industry averages, concentration by freezing requires only between ⅒ and ⅟₁₅ the energy required for water removal by conventional thermal evaporation. Actual cost analyses of concentration by several methods will be discussed in a later section.

A distinct advantage of freeze concentration is the low temperature difference between the liquid and the cooling medium. Few, if any, food liquids appear to be adversely affected by exposure to temperature below 0° C. for a short time. Some food liquids actually appear to benefit by such treatment. The low process temperatures also prevent degradation of heat-sensitive compounds. The food liquids can thus be concentrated without appreciable loss in taste, aroma, color, or nutritive value. Since the entire process is operated at or below the freezing temperature of water, and since vacuum treatment is not required, the loss of low boiling flavor and aromatic esters is almost completely avoided. Aromas are better retained in the juice and thus polymerization and condensation reactions of the aroma components, which may occur during aroma stripping in distillation, are fairly well inhibited. Volatile carryover is thus completely prevented in freeze concentration.

The use of steel vessels with aluminum heat transfer surfaces has been suggested, and PVC piping in seawater desalination and 316 stainless steel for concentration of corrosive chemicals.

The loss of soluble solids to the ice crystals could be avoided by proper monitoring of process parameters. Controlled crystallization allows formation of large, nearly pure ice crystals, and with adequate washing and recrystallization, dewatering could be made almost selective. Recycling a part of the ice melt and thus of any entrained solids to the crystallizer may also reduce solids losses. With modern processes, the solids losses have been reduced to less than 100 ppm. Unlike membrane separation processes, there is no danger of short circuiting the process by leaks.

In spite of the developments in water crystallography, there is always some loss of solids by entrainment in the crystals. As the solids are concentrated during freezing, the ice crystal size progressively decreases. The washing of the ice crystals therefore becomes more difficult and may require larger-diameter wash columns. The minimum desirable size of the ice crystals is reported to be 100 to 300 $\mu$m. Larger ice crystals can be grown by increasing the retention times of the feed in the crystallizer. This may, however, partially offset the overall-economics by lowering the output as well as increased energy requirements.

Since freeze concentration is capable of preserving almost all of the original chemical constituents, flavor, and aroma of fruit juices, the raw material should be of the highest quality. Thus, rigorous quality control of the feed material is required, ensuring that they are free of below-standard elements.

The use of freeze concentrating on pulpy products such as *Morinda citrifolia* has not heretofore been attempted.

Because of the strong gradient of freezing temperatures between the various components of the *Morinda citrifolia* pulp, there is a stepped gradient as the constituent components reach their freezing points. The benefits to this type of freezing are that components, upon freezing, may be removed and may be used to create products requiring different concentrates of *Morinda citrifolia*.

For example, since the most dilute components contain the most water and therefore freeze first, these components can be extracted from the solution by sifting the solid components from the liquid phase components and then can be either sold as a by-product or used as a dilute form of *Morinda citrifolia* in a beverage or to enhance a beverage. The more concentrated portions of the *Morinda citrifolia* slurry will freeze at a lower temperature and may then be extracted out to use as a concentrate in products such as cosmetics, therapeutic remedies, or in situations where it is expensive to ship a slurry in its liquid state.

Because the flavor and the therapeutic oils incorporated in the *Morinda citrifolia* slurry are not volatilized during the freeze concentrating process, the resulting concentrate still contains all of the health benefits of the slurry and also retains the flavor within the concentrate.

What is claimed is:

1. A method for freeze concentrating *Morinda citrifolia* comprising the steps of:

freezing, at a first temperature, a *Morinda citrifolia* slurry to effectuate a separation of pure water as ice crystals from said *Morinda citrifolia* slurry;

extracting said ice crystals from *Morinda citrifolia* slurry by sifting;

freezing, at a second temperature, the remaining non-aqueous constituents of said *Morinda citrifolia* slurry, wherein said second temperature is less than said first temperature; and recovering, from said remaining non-aqueous constituents of said Morinda citrifolia slurry, frozen, non-aqueous constituents wherein said recovered frozen, non-aqueous constituents frozen at said second temperature is concentrated Morinda citrifolia.

2. The method of claim 1, wherein said freezing at a second temperature occurs in gradients associated with freezing points of said remaining non-aqueous constituents of said *Morinda citrifolia* slurry.

3. The method of claim 1, wherein said recovered non-aqueous constituents comprise different concentrations of *Morinda citrifolia*.

4. The method of claim 1, wherein therapeutic oils indigenous to the *Morinda citrifolia* slurry are not volatilized during the method.

5. The method of claim 1, wherein said *Morinda citrifolia* slurry comprises flavor, and wherein said concentrated *Morinda citrifolia* retains said flavor.

6. The method of claim 1, wherein said *Morinda citrifolia* slurry comprises pulp.

7. The method of claim 1, wherein said *Morinda citrifolia* slurry comprises chemical constituents, and wherein performing said method allows the concentrated *Morinda citrifolia* to retain almost all of said chemical constituents.

8. A *Morinda citrifolia* concentrate obtained by the process of claim 1.

* * * * *